(12) United States Patent
Almulla et al.

(10) Patent No.: US 12,385,895 B2
(45) Date of Patent: Aug. 12, 2025

(54) ISOTOPIC MONITORING OF RESERVOIR WATER

(71) Applicant: SAUDI ARABIAN OIL COMPANY, Dhahran (SA)

(72) Inventors: Abdullah Almulla, Dhahran (SA); Bahi Mashat, Khobar (SA); Sattam Almutairi, Khobar (SA); Ranya Algeer, Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 343 days.

(21) Appl. No.: 18/054,593

(22) Filed: Nov. 11, 2022

(65) Prior Publication Data

US 2024/0159726 A1 May 16, 2024

(51) Int. Cl.
*G01N 33/18* (2006.01)
*E21B 49/08* (2006.01)
*G01N 33/28* (2006.01)

(52) U.S. Cl.
CPC ........... *G01N 33/18* (2013.01); *E21B 49/086* (2013.01); *G01N 33/2847* (2013.01)

(58) Field of Classification Search
CPC .. G01N 33/18; G01N 33/2847; E21B 49/086; E21B 43/00
See application file for complete search history.

(56) References Cited

U.S. PATENT DOCUMENTS

| | | |
|---|---|---|
| 5,979,228 A | 11/1999 | Brian et al. |
| 8,283,173 B2 | 10/2012 | Sukhijia et al. |
| 8,579,031 B2 | 11/2013 | Vinegar |
| 10,309,217 B2 | 6/2019 | Lawson et al. |
| 11,237,146 B2 | 2/2022 | Formolo et al. |
| 11,237,147 B2 | 2/2022 | Peterson et al. |

(Continued)

FOREIGN PATENT DOCUMENTS

| | | |
|---|---|---|
| CN | 107505228 A | 12/2017 |
| CN | 111649987 A | 9/2020 |

(Continued)

OTHER PUBLICATIONS

U.S. Appl. No. 63/391,823, filed Jul. 25, 2022, Yan; Chao.*

(Continued)

*Primary Examiner* — Timothy P Graves
(74) *Attorney, Agent, or Firm* — Vorys, Sater, Seymour and Pease LLP (57) ABSTRACT

The present disclosure relates to a method, including: collecting at least one water sample from a subterranean formation; obtaining a first normalized oxygen isotopic ratio based on a first water sample of the at least one water sample; obtaining a first normalized hydrogen isotopic ratio based on the first water sample; obtaining a first unknown water profile based on the first water sample, wherein the first unknown water profile comprises the first normalized oxygen isotopic ratio and the first normalized hydrogen isotopic ratio; comparing the first unknown water profile to at least one known water profile; and optimizing a hydrocarbon well, wherein optimizing a hydrocarbon well is based on comparing the first unknown water profile to at least one known water profile.

21 Claims, 3 Drawing Sheets

(56) References Cited

U.S. PATENT DOCUMENTS

| | | | | |
|---|---|---|---|---|
| 2010/0089142 A1* | 4/2010 | Sukhija | .................... | C09K 8/58 |
| | | | | 73/152.39 |
| 2014/0238670 A1* | 8/2014 | Pop | ........................ | E21B 49/10 |
| | | | | 166/264 |
| 2024/0027643 A1* | 1/2024 | Yan | .................... | G01N 33/2823 |

FOREIGN PATENT DOCUMENTS

| | | | |
|---|---|---|---|
| EP | 3032026 A1 | | 6/2016 |
| RU | 2571781 C1 | * | 12/2015 |

OTHER PUBLICATIONS

Mon-Lin Chou, Hong-Yang Tseng, Chung-Ho Wang, Zeng-Yei Hseu; Identification of the water source and groundwater recharge in a paddy field using stable hydrogen and oxygen isotopes. Water Supply Jul. 1, 2022; 22 (7): 6443â6457. doi: https://doi.org/10.2166/ws.2022.232 (Year: 2022).*

ISR-WO for PCT/US2023/037066 (which claims priority to this application) dated Mar. 6, 2024.

Chou et al. Identification of the water source and groundwater recharge in a paddy field using stable hydrogen and oxygen isotopes. Water Supply. Jun. 9, 2022, vol. 22, No. 7, pp. 1-15.

* cited by examiner

ISOTOPIC MONITORING OF RESERVOIR WATER

FIELD OF THE DISCLOSURE

The present disclosure relates generally to monitoring and management of hydrocarbon reservoirs and wells.

BACKGROUND OF THE DISCLOSURE

Hydrocarbon wells are bores designed to bring hydrocarbons to the surface for extraction and use in a variety of applications. A reservoir (a hydrocarbon well typically being located within a reservoir) is typically monitored for a variety of conditions in order to ensure optimal production rate and quality of product. Many tools may be used in order to measure reservoir conditions including temperature sensors, electromagnetic scanners, and acoustic telemetry equipment.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

A nonlimiting method according to the present disclosure may comprise: collecting at least one water sample from a subterranean formation; obtaining a first normalized oxygen isotopic ratio based on a first water sample of the at least one water sample; obtaining a first normalized hydrogen isotopic ratio based on the first water sample; obtaining a first unknown water profile based on the first water sample, wherein the first unknown water profile comprises the first normalized oxygen isotopic ratio and the first normalized hydrogen isotopic ratio; comparing the first unknown water profile to at least one known water profile; and optimizing a hydrocarbon well, wherein optimizing a hydrocarbon well is based on comparing the first unknown water profile to at least one known water profile.

Another nonlimiting method according to the present disclosure may comprise: collecting at least one water sample from a surface equipment of a hydrocarbon well, wherein the at least one water sample comprises condensed water, and wherein the hydrocarbon well comprises an offshore hydrocarbon well; obtaining a first normalized oxygen isotopic ratio based on a first water sample of the at least one water sample; obtaining a first normalized hydrogen isotopic ratio based on the first water sample; obtaining a first unknown water profile based on the first water sample, wherein the first unknown water profile comprises the first normalized oxygen isotopic ratio and the first normalized hydrogen isotopic ratio; logging the first unknown water profile to a data log; logging a second unknown water profile of the at least one unknown water profile to the data log; analyzing the first unknown water profile and the second unknown water profile using at least one known water profile; and optimizing the hydrocarbon well, wherein the hydrocarbon well is based on analyzing the first unknown water profile and the second unknown water profile.

Any combinations of the various embodiments and implementations disclosed herein can be used in a further embodiment, consistent with the disclosure. These and other aspects and features can be appreciated from the following description of certain embodiments presented herein in accordance with the disclosure and the accompanying drawings and claims.

DETAILED DESCRIPTION

Embodiments of the present disclosure will now be described in detail with reference to the accompanying Figures. Like elements in the various Figures may be denoted by like reference numerals for consistency. Further, in the following detailed description of embodiments of the present disclosure, numerous specific details are set forth in order to provide a more thorough understanding of the claimed subject matter. However, it will be apparent to one of ordinary skill in the art that the embodiments disclosed herein may be practiced without these specific details. In other instances, well-known features have not been described in detail to avoid unnecessarily complicating the description. Additionally, it will be apparent to one of ordinary skill in the art that the scale of the elements presented in the accompanying Figures may vary without departing from the scope of the present disclosure.

The present disclosure relates generally to monitoring and management of hydrocarbon reservoirs and wells. In particular, the present disclosure details methods for monitoring and management of hydrocarbon reservoirs through the analysis of isotopes in water collected from wells of a reservoir located within a subterranean formation. The water samples may be used to identify the source and type of water collected in order to identify the source of a breakthrough of formation water.

"Formation water," as used herein, refers to water that exists naturally within a subsurface formation or near a relevant portion of a subterranean formation during the exploration and drilling for hydrocarbons.

As used herein, "subsurface formation," or "subterranean formation," or simply "formation" refers to a geological feature below the surface (including a subsea surface) which may contain hydrocarbon resources therein. One or more of a "reservoir" or "hydrocarbon reservoir" may exist within a formation. Hydrocarbon resources may be contained within the reservoir that exists within a formation.

As used herein, "hydrocarbon well" or simply "well" refers to a boring in the surface (including a subsea surface) that is designed to bring hydrocarbons from a reservoir to the surface. "Hydrocarbons" include composites such as oil, natural gas, shale gas, and the like, as well as constituent molecules including methane, propane, ethane, and the like.

Formation water breakthrough to the well can be costly for operators of hydrocarbon wells, as it may reduce the operable life of a well and may limit production from the hydrocarbon well. Thus, tracking the source of water emerging from the well may allow for early detection and early intervention, prolonging the life of the well and saving costs and time for a well operator.

Traditionally, operators may use a deep borehole to obtain bottom-hole data concerning formation water; however, drilling for bottom-hole data can be costly. The present disclosure provides for methods that allow collection of water from existing well fluid transmission sources (including wellheads, flowlines, pipelines, and processing plants). "Well fluid" refers to any fluid originating from a well including hydrocarbons, as well as fluids such as fracturing fluids, produced water, and the like. Water collection in accordance with the present disclosure may save significant cost by allowing water to be collected where hydrocarbons are already flowing and thus reducing costly boring.

Figure 1:
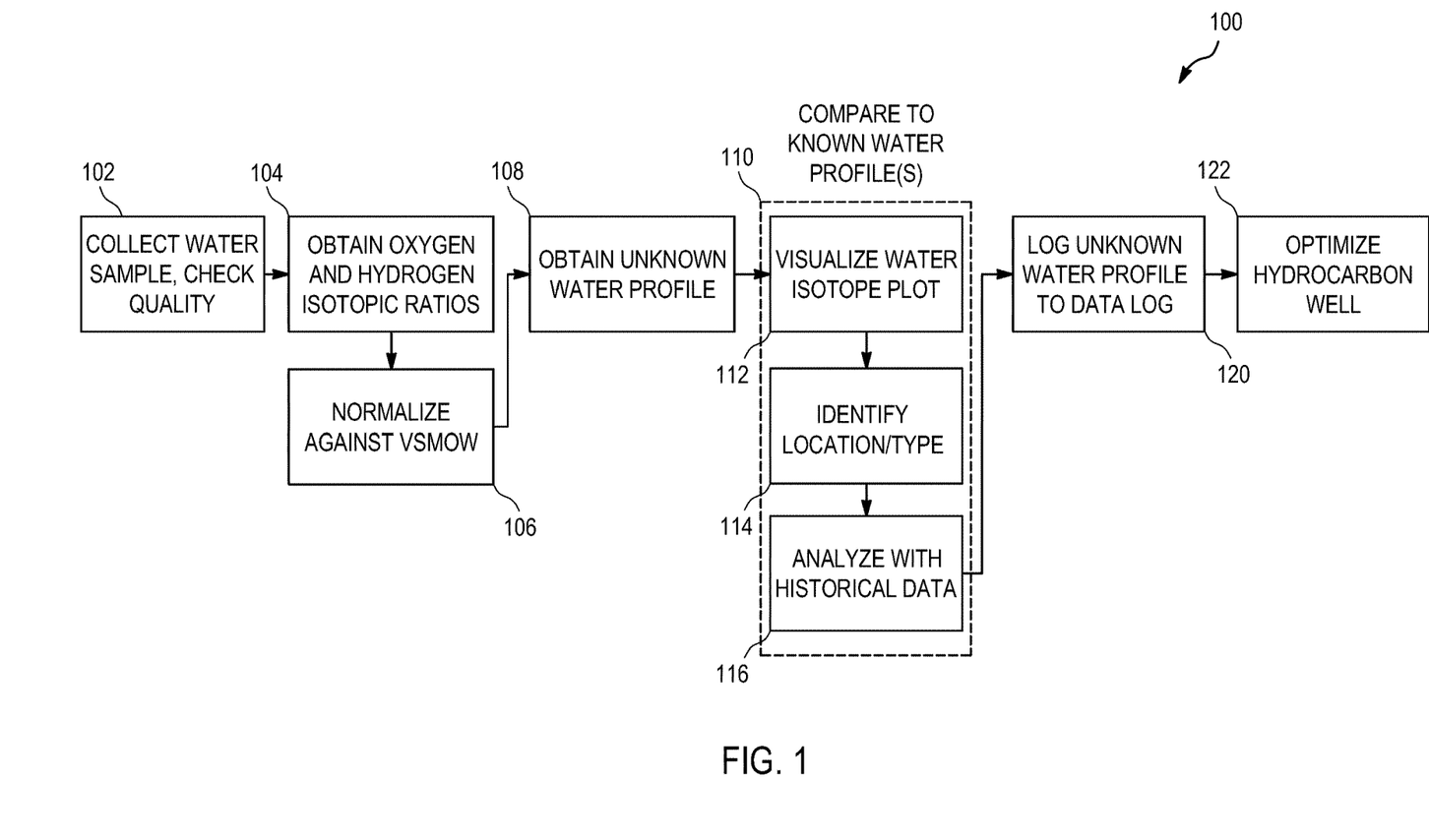
FIG. 1 is a flowchart depicting a nonlimiting method for isotopic analysis of reservoir water.

A method 100 for identifying water samples of the present disclosure is shown in FIG. 1. Water samples are collected and quality is checked 102. Subsequently an analyzer is used and isotopic ratios for oxygen and hydrogen are obtained 104. The ratios are normalized against Vienna Standard Mean Ocean Water (VSMOW) 106. Subsequently, an unknown water profile is obtained for the water sample 108.

The unknown water profile is compared to at least one known water profile at block 110. The comparison may include: visualizing water isotope plots 112, identifying a location and water type 114, and analyzing of the unknown water profile against historical water profile data at block 116. The unknown water profile may subsequently be logged to a data log at block 120. Finally, the information from the unknown water profile and its comparison to known water profile data may be used to optimize the hydrocarbon well 122. As a nonlimiting example, optimizing the hydrocarbon well may comprise planning for different completion techniques while drilling/producing in the hydrocarbon well. As another nonlimiting example, a gas well that has been identified as having water breakthrough can be re-completed with slimmer tubing to lift the remaining gas in the reservoir, avoiding major drilling costs to obtain reservoir bottom-hole data.

The at least one water sample may be collected during any phase of a well's lifecycle including drilling, completion, construction, flowback, production, and artificial lift.

Preferably, the collection of at least one water sample may occur during a flowback operation, and the at least one water sample may comprise well fluid removed from the reservoir. A "flowback operation" or simply "flowback" as used herein is a process performed as part of bringing a hydrocarbon well online. Flowback is performed after drilling and completion (including hydraulic fracturing or stimulation) of the well. During the flowback process, fluids used to drill, complete, and stimulate the well are removed from the reservoir. Flowback is also performed to test the capacity of flow of the well.

Collecting the at least one water sample may also preferably occur during a production stage of the well's life cycle.

In any stage of the well's life cycle, the at least one water sample from the well may be collected at any point on the surface or subsurface where fluids of the well or reservoir flow, including at a surface equipment. The surface equipment may include, a wellhead, a flowline, a pipeline a processing plant, or any other equipment which comprises within it fluid contents of the reservoir. Note that an individual water sample may be collected from a single location.

In some embodiments, the well from which the water sample originates may comprise a high pressure high temperature (HPHT) well. An HPHT well, as used herein, is defined as a well with an average bottom-hole temperature greater than 150° C. and a bottom-hole temperature greater than 10,000 psi. HPHT wells may produce a greater quantity of formation water than other wells and thus the application of the methods of the present disclosure to HPHT wells may allow for greater cost and time reduction than application of said methods to a non-HPHT well.

The well from which the water sample originates may comprise an onshore well or an offshore well. Offshore wells may produce a greater quantity of formation water than other wells and thus the application of the methods of the present disclosure to offshore wells may allow for greater cost and time reduction than application of said methods to an onshore well.

As part of the method within the present disclosure the at least one water sample may comprise condensed water. The collection of the at least one water sample may comprise collection of a condensed water sample.

A water sample (i.e., sample) in any method of the present disclosure may be collected by automated or manual means including sampling valves, sample containers, condensers, or any other suitable means. The water sample collected may comprise water in the form of a solid, a liquid, a gas, or any combination thereof, and may comprise impurities, additives, the like, or any combination thereof.

Figure 2:
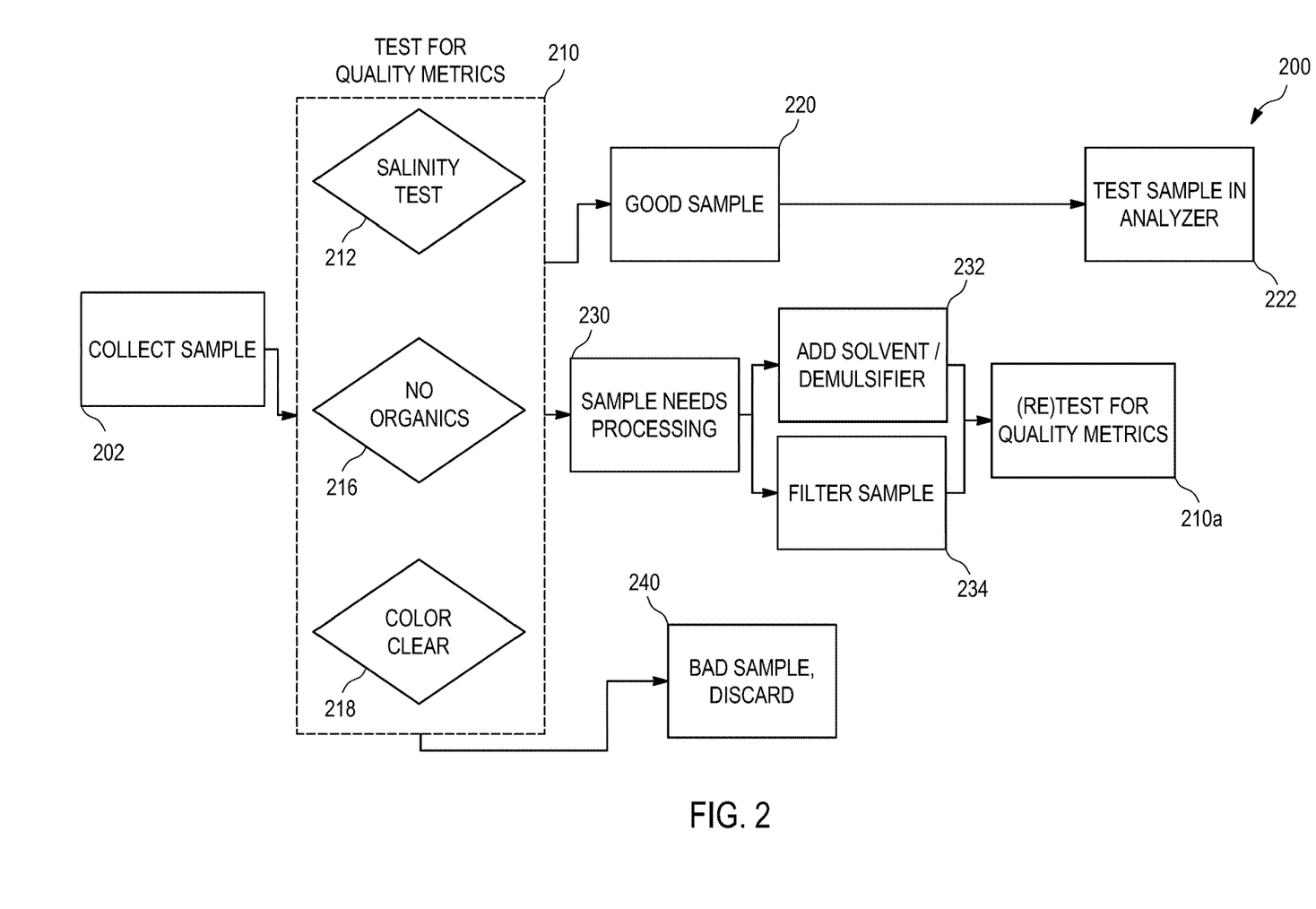
FIG. 2 is a flowchart depicting a nonlimiting method for testing quality metrics within the present disclosure.

For the collected water samples, a sample quality metric evaluation method may be used in accordance with the present disclosure as shown in the flowchart in FIG. 2. Following collection, a water sample may be tested for at least one quality metric according to inspection method 200. The collected sample 202 may be tested for quality metrics (i.e., at least one quality metric) 210. The testing may include criteria to pass including: a salinity test 212, no presence of organic materials 216, and clear color (indicating low or no impurities) 218. Salinity may be tested using an electric salinity meter probe to ensure it, preferably, does not exceed 200,000 ppm total dissolved solids (TDS) (or TDS may be less than 100,000 ppm, or less than 50,000 ppm, or less than 20,000 ppm, or less than 10,000 ppm, or less than 1,000 ppm). Organic material may be tested using an analyzer such as a laser spectroscopy analyzer. The organic material threshold may, preferably, be less than 5% by mass (or less than 10% by mass, or less than 15% by mass, or less than 4% by mass, or less than 3% by mass, or less than 2% by mass, or less than 1% by mass, or less than 0.1% by mass). Clear color may be tested visually by inspection of samples. Further suitable sampling means (e.g., online sampling, manual sampling, etc.) may be used to evaluate the at least one quality metric. Additional quality metrics may be utilized in accordance with the present disclosure.

The sample may undergo further processing 230. The further processing 230 may include wherein the water sample may have a solvent and/or demulsifier added to it 232. The solvent may comprise any suitable solvent known in the art including, but not limited to, propane, hexane, acetic acid, acetone, benzene, 1-butanol, chloroform, chlorobenzene, diethyl ether, ethanol, ethyl acetate, ethylene glycol, methanol, toluene, the like, or any combination thereof. The solvent may be preferably added at about a 1:1 ratio (or about 1:10, or about 1:100, or about 1:1000, or about 10:1, or about 100:1, or about 1000:1) to the sample, or any suitable ratio.

The demulsifier may comprise any suitable demulsifier including, but not limited to, an acid catalyzed phenol-formaldehyde resin, a base catalyzed phenol-formaldehyde resin, an epoxy resin, a polyethyleneimine, a polyamine, a diepoxide, a polyols, a dendrimer, the like, or any combination thereof. Suitable demulsifiers may be purchased from Schlumberger. The demulsifier may be preferably added at about a 1:1 ratio (or about 1:10, or about 1:100, or about 1:1000, or about 10:1, or about 100:1, or about 1000:1) to the sample, or any suitable ratio.

Further processing 230 may comprise filtering 234. The filter used may comprise a 0.45 μm filter or any suitable filter size. The water sample may be (re) tested for quality metrics 210a following processing of the sample 230. (Re) testing for quality metrics 210a may comprise one or multiple sub-blocks (i.e., 212, 216, and 218) within testing for quality metrics 210 in any combination. Blocks 210, 230, 232, 234, 210a, and any sub-blocks therein may each be repeated multiple times including 2 times, 3 times, 4 times, 5 times, or greater than 5 times, and may be repeated in any combination. For example, a sample may be collected at block 202, then filtered at 234, and subsequently tested for quality metrics at block 210, and further processed at block 230, and have a solvent added at block 232, and retested at block 210a.

If a sample does not pass testing for the at least one quality metric 210 including after (re) testing 210a the sample may be considered a bad sample and may be discarded 240.

If a sample passes testing for the at least one quality metric 210, the sample may be considered a good sample 220 and may be further tested in the analyzer 222.

Testing the water sample in the analyzer may comprise using a laser spectroscopy analyzer which can detect oxygen and hydrogen atomic abundance ratios (i.e., isotopic ratios). Any suitable laser spectroscopy analyzer capable of isotopic analysis of oxygen and hydrogen in water may be used. The isotopic ratios may include a $^{18}O/^{16}O$ ratio and a D/H ratio. $^{18}O$ refers to oxygen 18, i.e., oxygen with a mass number of 18, $^{16}O$ refers to oxygen 16, i.e., oxygen with a mass number of 16, D (or $^2H$) refers to deuterium (or hydrogen 2), i.e., hydrogen with a mass number of 2, and H (or $^1H$) refers to hydrogen 1, i.e., hydrogen with a mass number of 1.

Isotopic ratios of the oxygen in the water sample may be normalized against isotopic ratios of Vienna Standard Mean Ocean Water (VSMOW) for oxygen according to Equation 1 below.

$$\delta^{18}O(‰) = 1000\left[\frac{(^{18}O/^{16}O)_{SAMPLE}}{(^{18}O/^{16}O)_{VSMOW}} - 1\right] \quad \text{Equation 1}$$

where $\delta^{18}O$ (‰) is the normalized isotopic ratio for oxygen (18).

Similarly isotopic ratios of hydrogen in the water sample may be normalized against isotopic ratios of VSMOW for oxygen according to Equation 2 below.

$$\delta D(‰) = 1000\left[\frac{(D/H)_{SAMPLE}}{(D/H)_{VSMOW}} - 1\right] \quad \text{Equation 2}$$

where $\delta D$ (‰) is the normalized isotopic ratio for hydrogen (deuterium, i.e., hydrogen 2).

Values for VSMOW may be obtained from the International Atomic Energy Agency (IAEA), the (European) Institute for Reference Materials and Measurements (IRMM), the National Institute of Standards and Technology (NIST), or any suitable reference body.

Additional analysis may be performed by using liner fitting method to calculate a value for a sample in comparison to other samples, standards, or any combination thereof.

An unknown water profile for the water sample may be obtained. The unknown water profile may comprise a normalized hydrogen isotopic ratio and a normalized oxygen isotopic ratio. The unknown water profile may comprise other data in addition to isotopic ratio, including, but not limited to, timestamp, collection location, sample temperature, reservoir pressure, surface flowing pressure, formation water production flow rate, well productivity index, the like, or any combination thereof.

The unknown water profile may be compared to a known water profile (which may comprise multiple known water profiles). The comparing to a known water profile may comprise visualizing a water isotope plot. The water isotope plot may be created by plotting $\delta^{18}O$ (‰) on one axis of a two dimensional plot and $\delta D$ (‰) on the other axis of the two dimensional plot. Plotting may be performed using a manual means or any software suitable for graphical plotting such as MICROSOFT EXCEL® and the like.

The water isotope plot may allow for identification of a water type and a water source based on the known water profiles. The water type may comprise: surface water (e.g., lake water, river water, seawater) or subsurface water (e.g., formation water, non-formation water (e.g., aquifer water)). The water source may comprise a specific location within the subsurface or on the surface including a specific formation, lake, river, sea, and the like.

The data obtained from the unknown water profile may also be used to analyze the unknown water profile in relation to historical data comprising known water profile(s) collected from the same location or originating from the same well and/or the same subterranean formation. The analyzing of the unknown water profile in relation to historical data may comprise creating a water ingress trendline and may comprise plotting the unknown water profile on the water ingress trendline. The water ingress trendline may assist with well monitoring by visualizing the degree of ingress of formation water (including formation water breakthrough) for a well and/or formation.

The unknown water profile may be logged to a data log. The data log may comprise one or more unknown water profiles and one or more known water profiles. The data log may be stored using a manual means or any software or file type suitable for storing the water profile data.

Based on comparing the unknown water profile to the known water profile, the hydrocarbon well may be optimized. Optimizing the hydrocarbon well may comprise application of a formation water ingress (i.e., breakthrough) remediation method. Optimizing the hydrocarbon well may comprise re-completing the hydrocarbon well. Re-completing the well may occur with a tubing (wellbore piping) smaller in diameter than the previous tubing used to initially complete the well. The use of a smaller diameter tubing may, without being bound by theory, reduce the ingress of formation water.

Other formation water ingress remediation methods known in the art may be applied.

To facilitate a better understanding of the methods of the present disclosure, the following examples of preferred or representative embodiments are given. In no way should the following examples be read to limit, or to define, the scope of the disclosure.

EXAMPLES

Example 1

Water samples were collected from a flowline of an offshore well by condensing excess water from gas samples. Water samples were filtered using 0.45 μm filters to ensure that they were free of particulate organic matter or chemical additives. If a color persisted in water samples post the filtration step, the samples were treated by the addition of solvents (hexane and propane) and/or demulsifiers (purchased from Schulmberger), and retested against the quality metrics, and, optionally, filtered additionally.

Water samples were analyzed for oxygen and hydrogen isotopic ratios using a Picarro L2130-i Laser Cavity Ring-Down Spectroscopy (CRDS) instrument. The Picarro L2130-i Isotopic Water Analyzer contained the vaporizer, spectrometer, sample chamber, and an autosampler. A 5 ul of sample was injected into the vaporizer 8 times. The temperature (~110° C.) and the pressure (2.5±0.5 psig) were kept constant inside the line connecting the vaporizer to the spectrometer using 99.99% pure nitrogen gas addition and a heating element in the vaporizer. Constant temperature and pressure ensured total and instantaneous vaporization of the water without isotopic fractionation.

Figure 3:
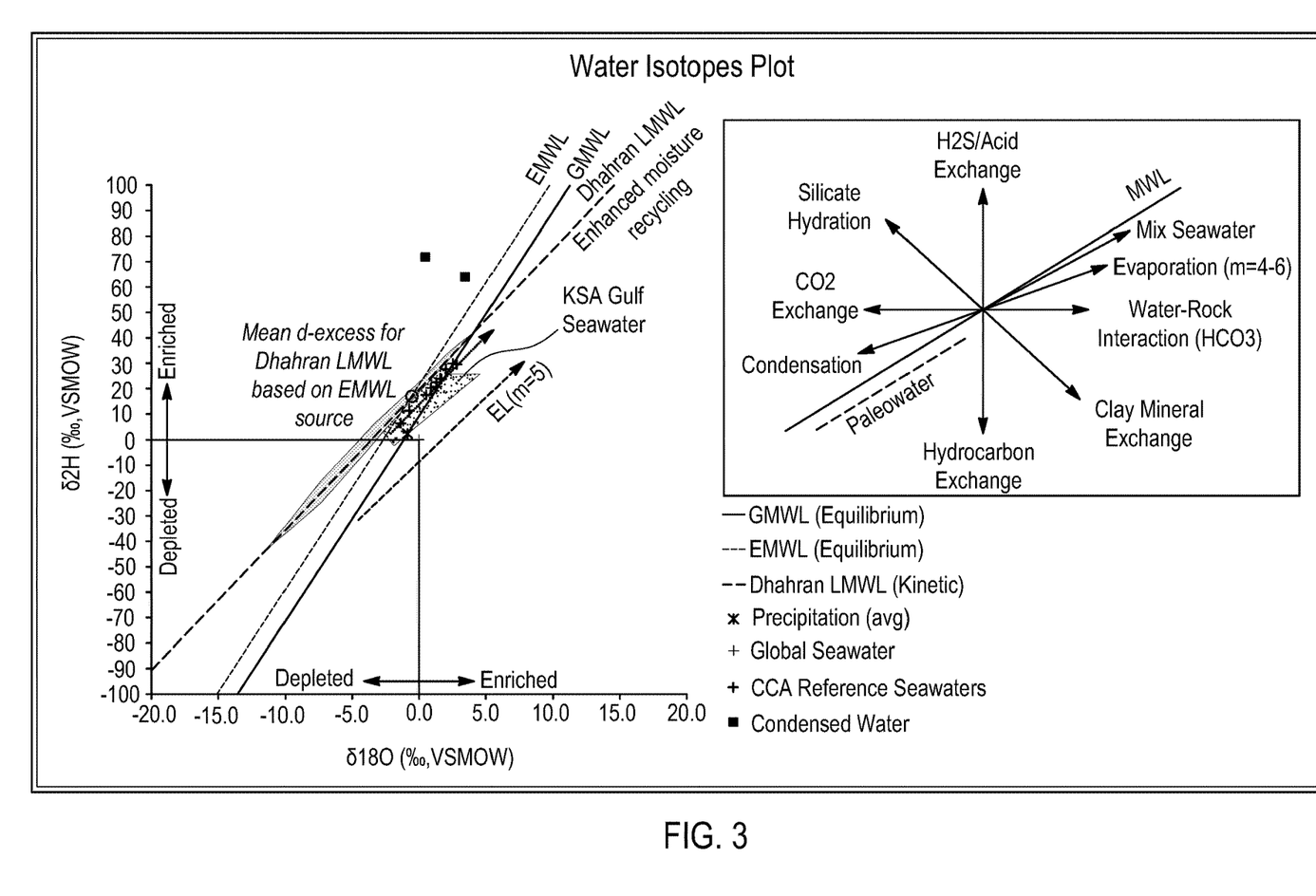
FIG. 3 is a nonlimiting example water isotopes plot.

After obtaining the isotopic ratios for oxygen and hydrogen, the isotopic ratios for the water samples were then normalized relative to Vienna Standard Mean Ocean Water (VSMOW) using delta notation ($\delta^{18}O$ and $\delta D$) to obtain an unknown water profile. The isotopic ratios of the unknown water profile were then plotted against known water profiles for reference data in a water isotopes plot, as illustrated in FIG. 3. Subsequently the source type and source location of the unknown water profile were able to be identified. The unknown water profile was then written to a data log.

ADDITIONAL EMBODIMENTS

Embodiments disclosed herein include:

Embodiment 1. A method comprising: collecting at least one water sample from a subterranean formation; obtaining a first normalized oxygen isotopic ratio based on a first water sample of the at least one water sample; obtaining a first normalized hydrogen isotopic ratio based on the first water sample; obtaining a first unknown water profile based on the first water sample, wherein the first unknown water profile comprises the first normalized oxygen isotopic ratio and the first normalized hydrogen isotopic ratio; comparing the first unknown water profile to at least one known water profile; and optimizing a hydrocarbon well, wherein optimizing a hydrocarbon well is based on comparing the first unknown water profile to at least one known water profile.

Embodiment 2. The method of Embodiment 1, wherein comparing the first unknown water profile to at least one known water profile comprises: identifying a water location for the first unknown water profile; and identifying a water type for the first unknown water profile.

Embodiment 3. The method of any one of Embodiments 1-2, wherein the water type comprises: surface water or subsurface water.

Embodiment 4. The method of Embodiments 3, wherein subsurface water comprises: formation water and non-formation water.

Embodiment 5. The method of any one of Embodiments 1-4, further comprising: logging the at least one unknown water profile of the at least one water sample in a data log.

Embodiment 6. The method of any one of Embodiments 1-5, wherein comparing the first unknown water profile to at least one known water profile comprises visualizing a water isotope plot.

Embodiment 7. The method of any one of Embodiments 1-6, wherein the at least one known water profile originates from the subterranean formation.

Embodiment 8. The method of any one of Embodiments 1-7, wherein comparing the first unknown water profile to at least one known water profile comprises: creating a water ingress trendline; and plotting the first unknown water profile on the water ingress trendline.

Embodiment 9. The method of any one of Embodiments 1-8, wherein optimizing a hydrocarbon well comprises: identifying a water breakthrough.

Embodiment 10. The method of any one of Embodiments 1-9, wherein optimizing a hydrocarbon well comprises: re-completing the hydrocarbon well.

Embodiment 11. The method of any one of Embodiments 1-10, wherein obtaining a first oxygen-18 delta value or obtaining a first deuterium-2 delta value comprises analyzing the first water sample using a laser spectroscopy analyzer.

Embodiment 12. The method of any one of Embodiments 1-11, wherein obtaining a first oxygen-18 delta value or obtaining a first deuterium-2 delta value comprises normalizing relative to Vienna Standard Mean Ocean Water (VSMOW).

Embodiment 13. The method of any one of Embodiments 1-12, wherein the at least one water sample comprises condensed water.

Embodiment 14. The method of any one of Embodiments 1-13, wherein collecting at least one water sample from a subterranean formation occurs during a flowback operation.

Embodiment 15. The method of any one of Embodiments 1-14, wherein collecting each of the at least one water sample from a subterranean formation occurs at a surface equipment, and wherein the surface equipment comprises: a wellhead, a flowline, a pipeline, or a processing plant.

Embodiment 16. The method of any one of Embodiments 1-15, further comprising: inspecting the first water sample for at least one quality metric.

Embodiment 17. The method of Embodiment 16, wherein the at least one quality metric comprises: a presence of organic materials, a salinity, or a color.

Embodiment 18. The method of any one of Embodiments 1-17, further comprising: adding a solvent to the first water sample; and/or adding a demulsifier to the first water sample; and/or filtering the first water sample.

Embodiment 19. The method of any one of Embodiments 1-18, wherein the hydrocarbon well comprises a high pressure high temperature (HPHT) well.

Embodiment 20. The method of any one of Embodiments 1-19, wherein the hydrocarbon well comprises an offshore well.

Embodiment 21. A method comprising: collecting at least one water sample from a surface equipment of a hydrocarbon well, wherein the at least one water sample comprises condensed water, and wherein the hydrocarbon well comprises an offshore hydrocarbon well; obtaining a first normalized oxygen isotopic ratio based on a first water sample of the at least one water sample; obtaining a first normalized hydrogen isotopic ratio based on the first water sample; obtaining a first unknown water profile based on the first water sample, wherein the first unknown water profile comprises the first normalized oxygen isotopic ratio and the first normalized hydrogen isotopic ratio; logging the first unknown water profile to a data log; logging a second unknown water profile of the at least one unknown water profile to the data log; analyzing the first unknown water profile and the second unknown water profile using at least one known water profile; and optimizing the hydrocarbon well, wherein the hydrocarbon well is based on analyzing the first unknown water profile and the second unknown water profile.

Embodiment 22. The method of Embodiment 21, wherein the surface equipment comprises: a wellhead, a flowline, a pipeline, or a processing plant.

The terminology used herein is for the purpose of describing particular embodiments only and is not intended to be limiting of the invention. As used herein, for example, the singular forms "a," "an," and "the" are intended to include the plural forms as well, unless the context clearly indicates otherwise. It will be further understood that the terms "contains," "containing," "includes," "including," "comprises," and/or "comprising," and variations thereof, when used in this specification, specify the presence of stated features, integers, steps, operations, elements, and/or components, but do not preclude the presence or addition of one or more other features, integers, steps, operations, elements, components, and/or groups thereof.

Terms of orientation are used herein merely for purposes of convention and referencing and are not to be construed as limiting. However, it is recognized that these terms could be used with reference to an operator or user. Accordingly, no limitations are implied or to be inferred. In addition, the use of ordinal numbers (e.g., first, second, third, etc.) is for distinction and not counting. For example, the use of "third" does not imply there must be a corresponding "first" or "second." Also, if used herein, the terms "coupled" or "coupled to" or "connected" or "connected to" or "attached" or "attached to" may indicate establishing either a direct or indirect connection, and is not limited to either unless expressly referenced as such.

While the disclosure has described several exemplary embodiments, it will be understood by those skilled in the art that various changes can be made, and equivalents can be substituted for elements thereof, without departing from the spirit and scope of the invention. In addition, many modifications will be appreciated by those skilled in the art to adapt a particular instrument, situation, or material to embodiments of the disclosure without departing from the essential scope thereof. Therefore, it is intended that the invention not be limited to the particular embodiments disclosed, or to the best mode contemplated for carrying out this invention, but that the invention will include all embodiments falling within the scope of the appended claims. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative.

What is claimed is:

1. A method comprising:
    collecting at least one water sample from a subterranean formation;
    obtaining a first normalized oxygen isotopic ratio based on a first water sample of the at least one water sample;
    obtaining a first normalized hydrogen isotopic ratio based on the first water sample;
    obtaining a first unknown water profile based on the first water sample, wherein the first unknown water profile comprises the first normalized oxygen isotopic ratio and the first normalized hydrogen isotopic ratio;
    comparing the first unknown water profile to at least one known water profile, wherein comparing the first unknown water profile to at least one known water profile comprises:
        creating a water ingress trendline; and
        plotting the first unknown water profile on the water ingress trendline; and
    optimizing a hydrocarbon well, wherein optimizing a hydrocarbon well is based on comparing the first unknown water profile to at least one known water profile.

2. The method of claim 1, wherein comparing the first unknown water profile to at least one known water profile comprises:
    identifying a water location for the first unknown water profile; and
    identifying a water type for the first unknown water profile.

3. The method of claim 2, wherein the water type comprises: surface water or subsurface water.

4. The method of claim 3, wherein subsurface water comprises: formation water and non-formation water.

5. The method of claim 1, further comprising:
    logging the at least one unknown water profile of the at least one water sample in a data log.

6. The method of claim 1, wherein comparing the first unknown water profile to at least one known water profile comprises visualizing a water isotope plot.

7. The method of claim 1, wherein the at least one known water profile originates from the subterranean formation.

8. The method of claim 1, wherein optimizing a hydrocarbon well comprises: identifying a water breakthrough.

9. The method of claim 1, wherein optimizing a hydrocarbon well comprises: re-completing the hydrocarbon well.

10. The method of claim 1, wherein obtaining the first normalized oxygen isotopic ratio or obtaining the first normalized hydrogen isotopic ratio comprises analyzing the first water sample using a laser spectroscopy analyzer.

11. The method of claim 1, wherein obtaining the first normalized oxygen isotopic ratio or obtaining the first normalized hydrogen isotopic ratio comprises normalizing relative to Vienna Standard Mean Ocean Water (VSMOW).

12. The method of claim 1, wherein the at least one water sample comprises condensed water.

13. The method of claim 1, wherein collecting at least one water sample from a subterranean formation occurs during a flowback operation.

14. The method of claim 1, wherein collecting each of the at least one water sample from a subterranean formation occurs at a surface equipment, and wherein the surface equipment comprises: a wellhead, a flowline, a pipeline, or a processing plant.

15. The method of claim 1, further comprising:
    inspecting the first water sample for at least one quality metric.

16. The method of claim 15, wherein the at least one quality metric comprises: a presence of organic materials, a salinity, or a color.

17. The method of claim 1, further comprising:
    adding a solvent to the first water sample; and/or
    adding a demulsifier to the first water sample; and/or
    filtering the first water sample.

18. The method of claim 1, wherein the hydrocarbon well comprises a high pressure high temperature (HPHT) well.

19. The method of claim 1, wherein the hydrocarbon well comprises an offshore well.

20. A method comprising:
collecting at least one water sample from a surface equipment of a hydrocarbon well, wherein the at least one water sample comprises condensed water, and wherein the hydrocarbon well comprises an offshore hydrocarbon well;
obtaining a first normalized oxygen isotopic ratio based on a first water sample of the at least one water sample;
obtaining a first normalized hydrogen isotopic ratio based on the first water sample;
obtaining a first unknown water profile based on the first water sample, wherein the first unknown water profile comprises the first normalized oxygen isotopic ratio and the first normalized hydrogen isotopic ratio;
logging the first unknown water profile to a data log;
logging the first unknown water profile to a data log;
obtaining a second normalized oxygen isotopic ratio based on a second water sample of the at least one water sample;
obtaining a second normalized hydrogen isotopic ratio based on the second water sample;
obtaining a second unknown water profile based on the second water sample, wherein the second unknown water profile comprises the second normalized oxygen isotopic ratio and the second normalized hydrogen isotopic ratio;
logging the second unknown water profile of the at least one unknown water profile to the data log;
analyzing the first unknown water profile and the second unknown water profile using at least one known water profile, wherein analyzing the first unknown water profile and the second unknown water profile using at least one known water profile comprises:
creating a water ingress trendline; and
plotting the first unknown water profile and the second unknown water profile on the water ingress trendline; and
optimizing the hydrocarbon well, wherein the hydrocarbon well is based on analyzing the first unknown water profile and the second unknown water profile.

21. The method of claim 20, wherein the surface equipment comprises: a wellhead, a flowline, a pipeline, or a processing plant.

* * * * *